(12) United States Patent
Mullejeans et al.

(10) Patent No.: US 8,013,206 B2
(45) Date of Patent: Sep. 6, 2011

(54) DEVICE FOR RECORDING AND TRANSFERRING A CONTOUR

(75) Inventors: Peter Mullejeans, Aalsgaarde (DK); Betina Toelboell Nielsen, Kvistgaard (DK)

(73) Assignee: Coloplast A/S, Humlebaek (DK)

( * ) Notice: Subject to any disclaimer, the term of this patent is extended or adjusted under 35 U.S.C. 154(b) by 348 days.

(21) Appl. No.: 11/920,738

(22) PCT Filed: May 19, 2006

(86) PCT No.: PCT/DK2006/000277
§ 371 (c)(1), (2), (4) Date: Nov. 20, 2007

(87) PCT Pub. No.: WO2006/122565
PCT Pub. Date: Nov. 23, 2006

(65) Prior Publication Data
US 2009/0234313 A1    Sep. 17, 2009

(30) Foreign Application Priority Data

May 20, 2005  (DK) ................................. 2005 00734

(51) Int. Cl.
*A61F 13/00* (2006.01)
(52) U.S. Cl. .......................................... 602/41; 602/42
(58) Field of Classification Search .............. 602/42–56; 128/888, 889; 604/304, 307
See application file for complete search history.

(56) References Cited

U.S. PATENT DOCUMENTS

| | | | | |
|---|---|---|---|---|
| 4,107,861 A | * | 8/1978 | Johnson ..................... 40/654.01 |
| 4,787,380 A | * | 11/1988 | Scott ............................... 602/52 |
| 5,265,605 A | * | 11/1993 | Afflerbach .................... 600/300 |
| 5,605,165 A | * | 2/1997 | Sessions et al. .............. 128/888 |
| 6,359,100 B1 | * | 3/2002 | Hostettler et al. .............. 528/58 |
| 6,659,989 B1 | | 12/2003 | Otto | |

FOREIGN PATENT DOCUMENTS

| | | |
|---|---|---|
| DE | 1 008 105 | 5/1957 |
| EP | 0 640 332 A1 | 3/1995 |
| EP | 0 730 845 A2 | 9/1996 |
| EP | 1 124 516 | 8/2001 |
| JP | 2-23965 | 6/1995 |
| JP | 7-163526 | 6/1995 |
| WO | WO 00/25709 | 5/2000 |

* cited by examiner

*Primary Examiner* — Michael Brown
(74) *Attorney, Agent, or Firm* — Coloplast Corp., Coloplast A/S; Daniel G. Chapik; Nicholas R. Baumann

(57) ABSTRACT

The invention relates to a device for recording and transferring the contours of a wound or opening in tissue of a human being comprising a transparent polymer sheet having a first and a second surface, wherein the first surface faces the wound or opening and the second surface comprises a central portion and an edge portion wherein the edge portion is provided with an adhesive layer. The device is placed over the wound or opening and the contours are traced on the central portion of the device, then the device is reversed and transferred to an appliance, and an aperture is cut from the traced contours.

7 Claims, 4 Drawing Sheets

DEVICE FOR RECORDING AND TRANSFERRING A CONTOUR

This is a national stage of PCT/DK06/000277 filed May 19, 2006 and published in English.

BACKGROUND OF THE INVENTION

1. Field of the Invention

The invention relates to a device for appliances for ostomy, fistula, wound or drain site treatment.

In connection with surgery for a number of diseases in the gastrointestinal tract a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

Wafers of appliances for ostomy, fistula, wound or drain site treatment are manufactured in a variety of different standard shapes, sizes and configurations to meet the many different needs of the users. Although these standard products meet the needs of the average user, they do not ideally meet the needs of any particular individual. In most cases, the user must adapt the product prior to use to suit his or her anatomy or lifestyle. Typical modifications, which can be performed include cutting of the aperture in the wafer for receiving the wound or opening in tissue the wafer. Where the aperture for a stoma may be substantially the same for the same patient and thus a number of wafers may be provided with an aperture custom made for this particular patent, a wound or fistulae may change contours and size over time and thus a new customized aperture has to be made for each appliance.

2. Description of the Related Art

Methods for recording the size and shape of wounds are well known:

In EP patent application No. EP 730 845 is disclosed a device for measuring wound surface. The device is in the form of a transparent sheet being folded to provide two superimposed sheets. A perforated line may separate the sheets from each other's. The double layer is placed over the wound; the contours of the wound are marked with a marking device on the top layer. Then the second layer, facing the wound and being smeared by wound exudates, are removed by tearing along the perforated line. The sheet with the markings is saved in the patients file.

U.S. Pat. No. 5,265,605 discloses a wound assessment tool in the form of a first transparent sheet, adhered to a second transparent sheet. The combined sheets are placed over the wound, the contours of the wound are marked up on the upper sheet, and then the lower sheet is removed and discarded, and the upper sheet, with the drawing of the wound, is saved for the record in the patients file.

EP patent application No. EP 640 332 discloses a wound dressing in a package, wherein the package may be used as a wound assessment tool. One side of the package serves as a protection layer against exudates from the wound while the other layer is for recording the size of the wound. The protection layer is discarded after use and the record layer is saved for the file.

None of the above-mentioned references provides a method for transferring the image of the wound to an appliance, on the contrary, if they were used for this purpose a mirror image would occur on the appliance, which would be unusable for this purpose.

Methods for preparing customized apertures in ostomy appliances are also known. In EP Patent No. 1 124 516 is disclosed a method for making a customized ostomy appliance comprising the steps of: measuring the outer contour of the stoma of the patient, recording the information relating to the measurements and transforming the recorded information into electronic form, and utilizing the information for printing a cutting guide pattern on a material for adhering to the adhesive wafer of the appliance. The method is only applicable when a large number of identical apertures are desired.

Thus there is still a need for a device for recording and transferring an image of a wound or opening in tissue to an appliance for ostomy, fistula, wound or drain site treatment.

SUMMARY OF THE INVENTION

It is an object of the present invention to be able to trace the contours of a wound or opening and transfer the tracing in an easy and accurate manner to an appliance.

It is further an object of the present invention to provide a method for tracing and transferring an image of a wound or opening.

It is still further an object of the present invention to provide an appliance with a customized aperture for receiving a wound or opening.

BRIEF DESCRIPTION OF THE DRAWINGS

The invention is disclosed more in detail with reference to the drawings in which.

DETAILED DESCRIPTION OF THE PRESENT INVENTION

Figure 1:
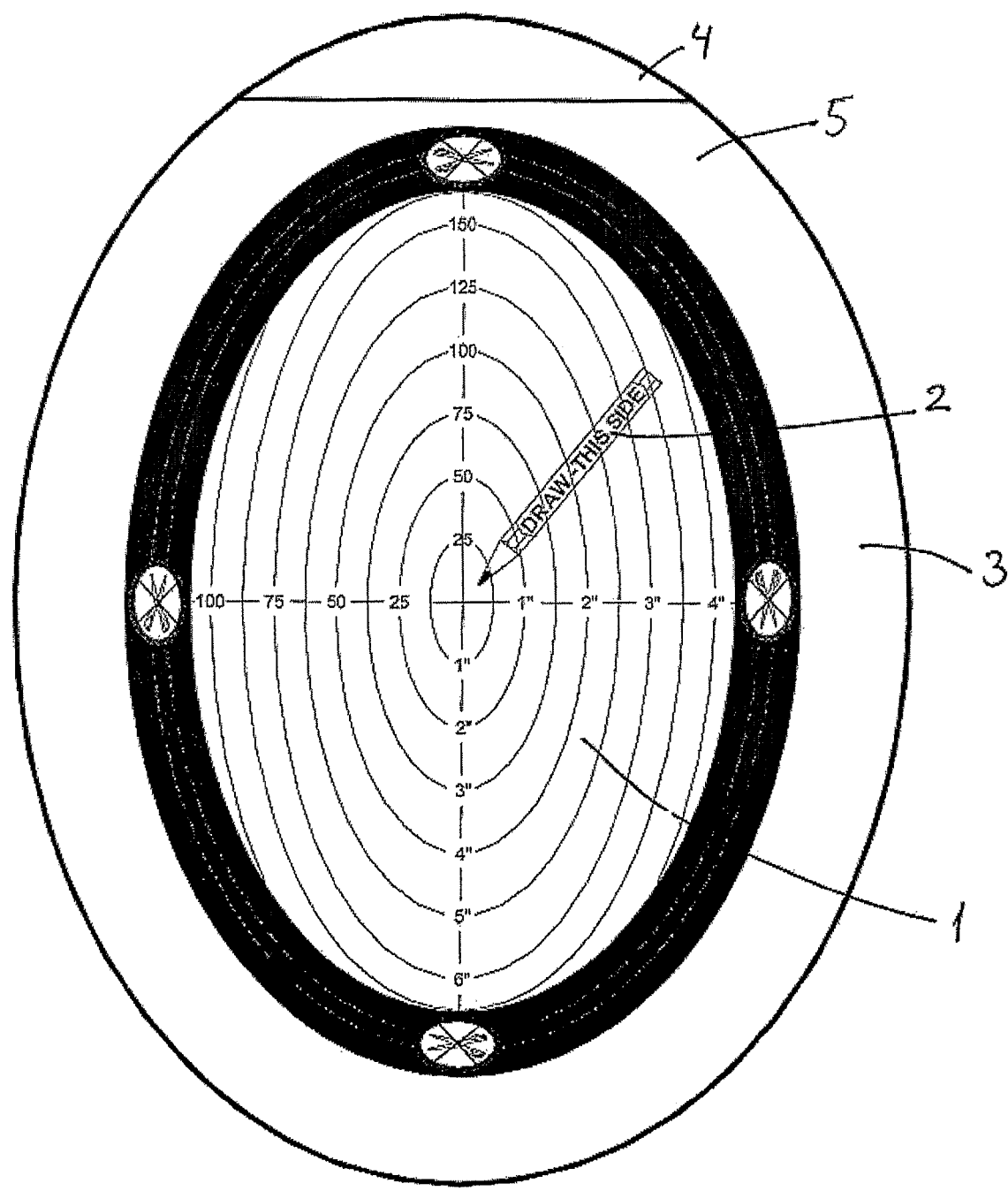
FIG. 1 shows a preferred embodiment of the invention seen from the non-skin facing side.

The invention relates to a device for recording the contours of a wound or opening in tissue of a human being comprising a transparent polymer sheet having a first and a second surface, wherein the first surface faces the wound or opening and the second surface comprises a central portion and an edge portion wherein the edge portion is provided with an adhesive layer.

By suitable for drawing is meant a surface to which it is possible to draw with e.g. a speed marker, pencil, ball-pen or other drawing tools. Some surfaces, e.g. coatings such as Teflon may repel any kind of drawing tools, the ink will glance off, and such surface would be unsuitable for drawing.

Devices for recording size and shapes of wounds or openings in tissue often suffer from the drawback that the size is recorded by placing a transparent sheet over the wound or opening, tracing the outline of the wound or opening and then mounting the sheet on the skin-facing surface of an adhesive wafer of a collection bag. However, in doing so, the transferred image will be mirrored on the wafer. Working with ostomy openings this may be a minor problem as these may be substantially round or symmetric, but in the handling of wounds or fistulae, the contours may be quite asymmetric and irregular, thus a mirror image may not fit at all.

A way of avoiding this mirror image is to trace the contours of the wound onto a transparent sheet, cutting the sheet along the contours, reversing the sheet and use it as a template for drawing the mirror-image on the wafer and then cutting the wafer. However, this method may be laborious and inaccurate.

A record of the contours of a wound or opening may be transferred to the non-skin-facing surface of the wafer, thus the mirror problem is avoided. However, this surface of the wafer is usually occupied by coupling means and/or collection bags and is thus highly unsuitable for this use.

In the treatment of wounds or fistulae, it is important the wafer of the appliance is fitting precisely around the wound or opening. If the aperture is too large, the effluent from the wound or opening may soak the surrounding healthy skin, thus giving rise to maceration of the skin, furthermore while washing/cleaning of the wound the washing fluids may also damage the skin. So, a snug fit around the wound or opening is crucial.

By using the device of the present invention it has surprisingly been shown that an accurate record of the wound or opening may be obtained and transferred to the adhesive wafer of appliance.

The present invention improves the precision of transferring the contours of a wound from a patient to a product as the recorded contours may be used directly for cutting without being redrawn.

Furthermore, the invention simplifies the work, makes it easier for the user to transfer the contours of a wound or opening from a patient to an appliance.

The present invention makes it unnecessary to apply a label or a print onto the backing of an application, as all the necessary inscriptions can be applied to the application by attaching the device of the invention to the application.

The second surface, facing away from the wound is adapted to be marked upon, by tracing the outline of the wound or opening. For tracing a marking pen or other suitable device may be used. Preferably the central portion is non-adherent.

In order to avoid wrong use of the sheet, the wound facing surface may be provided with properties, e.g. in the form of a coating which renders it difficult or impossible to mark upon. Such coating may be in the form of a silicone, Teflon or the like. Or the sheet may be in the form of a laminate where the material of the second surface has inherent properties for repelling ink or the like. The user will note that the making pen is not able to draw on the coated surface when it is used in the wrong position, and thus the user may turn it upside down into correct position and continue tracing.

The adhesive layer may be in the form of a pattern of adhesive and non-adhesive areas or it may be in the form of a homogenous coating. As the function of the adhesive is to hold the sheet fixed to the adhesive wafer during cutting or transfer of the contours, the amount and distribution of the adhesive is not restricted to any particular form as long as the function of fixating the sheet to the wafer is present. The adhesive layer may e.g. be in the form of separate or connected dots or lines of adhesive. The skin-facing surface of the adhesive wafer may typically be provided with a protective release liner, such as a siliconised paper to be removed before application to the body part. The device of the invention may be attached to this release liner before cutting.

After cutting, the release liner on the adhesive wafer may then be removed together with the device of the invention and saved as documentation of the patients wound condition historically.

The adhesive may in one embodiment of the invention be in the form of a low tack adhesive, i.e. a "post-it" adhesive which may be attached and detached several times. This opens for the possibility of repositioning the sheet for correction, and after cutting to remove the sheet from the wafer and store it in the patients record. The storage of the record may also be achieved by removing the release liner of the wafer, carrying the sheet and store this laminate in the file.

It is preferred that the sheet, especially the central portion, is having indicia thereon which allows a user to determine the contours of a wound. The indicia may be in the form of a grid or a bulls-eye or other kind of suitable markings, helping the user to correct positioning of the sheet and accurate tracing of contours of the wound or opening.

The sheet may be prepared from any suitable transparent material. In order to see the contours of the wound through the material, it has to be provided with a certain transparency or translucency. The hereby used "transparent" is to be interpreted as translucent enough to render the contours of the wound or opening traceable looking through the sheet. Thus a slightly opaque material may also be used. A certain flexibility of the sheet may also be desired as the sheet may be applied to curved body parts such as abdomen, sacrum, arms or legs. The sheet may preferably be prepared from a transparent polymer being selected from the group consisting of polypropylene, polyurethane, polyethylene, polyvinylchloride, polyester, polystyrene and acetate.

The adhesive layer of the second surface may be protected by at least one release liner. The release liner may cover the adhesive layer but not the central portion of the sheet, as this would inhibit the marking process. In a preferred embodiment of the invention the device comprises at least two release liners, a first liner exposing a small area of the adhesive layer when removed, and a second liner covering a the residual surface of the adhesive layer. The first liner may be removed first and the sheet is positioned at the adhesive wafer. When correct positioning is achieved, the adhesive maintains the position and then the second liner is removed and the device is adhered to the wafer.

Thus, a first release liner may be present for exposing only a small area of the adhesive layer. This is done to make it easier for the user to achieve correct position of the device onto the wafer.

In one embodiment of the invention the entire second surface of the present invention is provided with an adhesive coating, but the central portion is further provided with a non-adhesive, transparent layer, suitable for drawing. The non-adhesive transparent layer may cover the entire adhesive surface of the second layer, but the central portion and the edge portion of this non-adhesive transparent layer may be parted, e.g. by kiss-cutting a line separating the two portions. The non-adhesive transparent layer part covering the edge portion may thus serve as protective release liner for the adhesive, while the center portion of said layer may be used for drawing. This embodiment of the invention facilitates easy production of the device.

The first surface is provided with a transparent protection layer. The protection layer serves to protect the sheet from getting smudgy by the exudates from the wound or opening, and is used during marking up the wound or opening and then removed and discarded before applying the device to the wafer. The protective layer may be in the form of a separate layer or it may be attached to the sheet. Attachment may be in the form of adhesive or welding along the edge portion or a continuation of the sheet being folded and preferably provided with a tear line for separation the two layers. In one embodiment of the invention the protective layer is adhered without application of adhesive but utilizing inherent adhesive properties of the material, e.g. like cling-film. The protective layer may be substantially the same size as the device of the invention or it may be larger.

The Invention further relates to a method for recording the contours of a wound or opening in the tissue of a human being comprising the steps of:
   a) covering the wound or opening with a transparent polymer sheet having a first and a second surface, wherein the first surface faces the wound or opening and the second surface comprises a central portion and an edge portion wherein the edge portion is provided with an adhesive layer,
   b) tracing the contours of the wound or opening on the central portion of the second surface of the sheet,
   c) removing the sheet from the wound or opening,
   d) attaching the adhesive layer of the second surface of the sheet to the skin-facing surface of an adhesive wafer of an appliance for ostomy, fistula, wound or drain site treatment,
   e) cutting an aperture in the adhesive wafer for receiving the wound or opening.

When the wafer has been cut the polymer sheet of the invention may be removed from the wafer and saved for the patients file. In one embodiment of the Invention the sheet is removed together with the release liner of the adhesive wafer.

Preferably, a transparent protection layer is placed between the wound and the transparent sheet in order to avoid smudging of the sheet. The protection layer may be a part of the device of the invention or it may be a separate layer.

The invention further relates to a kit comprising an appliance for ostomy, fistulae, wound or drain site treatment and a transparent polymer sheet having a first and a second surface, wherein the first surface faces the wound or opening and the second surface comprises a central portion and an edge portion wherein the edge portion is provided with an adhesive layer.

The central portion is preferably non-adherent in order to facilitate marking of the wound or opening.

The adhesive layer may be in the form of a pattern of adhesive and non-adhesive areas.

The central portion has preferably indicia thereon which allows a user to determine the contours of a wound. The indicia may be in the form of a printed pattern such as a grid or bull-eye.

The transparent polymer may preferably be selected from the group consisting of polypropylene, polyurethane, polyethylene, polyvinylchloride, polyester, polystyrene and acetate.

The adhesive layer may be protected by at least one release liner.

The kit may further enclose a transparent protection layer for placing between the first surface of the sheet and the wound or opening. The protection layer may be in the form of a transparent cover or film, which is placed over the patient in order to prevent any exudates from the wound or opening from getting in contact with the polymer sheet. Hereby the hygienically status of the product is preserved.

By using the kit of the present invention for tracing the size of a wound or opening, the work will be eased for the user and the accuracy of the transfer of the markings will be improved.

When the contours of the wound or opening have been marked up on the transparent polymer sheet, the sheet constitutes a piece of documentation showing cut-zone information and size of wound.

In order to prevent the user in turning the device upside down when tracing the contours of the wound, the first surface of the sheet may be provided with a description or an illustration, illustrating the user which side to orientate upwards before drawing onto it. Furthermore, the first surface of the sheet may be siliconised or treated in other way in order to make the surface repel the marking tool. The same material characteristic may be obtained by using a laminate material having different properties for each surface. Thus, it may be prevented that the user traces the contours of the wound or opening to the wrong side of the sheet.

The device of the present invention may further more be provided with a description or illustration that informs the user about the boundaries for where to cut or not to cut, grid for measuring the width and the length of a wound, marked space for writing initials of patient, date of treatment etc.

The central portion of the second surface of the device of the present invention is prepared from a transparent or translucent film material that can be drawn on with a permanent pen, Indian ink or other form of marking pens without being able to smear off easily.

This second surface of the flexible transparent sheet is preferably provided with a central non-adhesive portion and a peripheral adhesive portion.

The central, non-adhesive portion is preferably not covered by a release liner. The adhesive portion is preferably covered by at least one release liner that does not cover the portion of the surface that the user may provide with markings.

After having attached the transparent polymer sheet onto the skin-facing surface of the wafer, the user then may cut the laterally reversed markings with e.g. a pair of scissors or a knife directly through the sheet.

The use of these means will ease the work and improve accuracy in transferring a drawing of a wound or opening onto a wafer for ostomy, fistula, wound or drain site treatment.

The use of these means will make it unnecessary to apply any label or print onto the application, where the necessary inscriptions can be applied onto the application secondary. The aperture is cut directly from the recorded contour, the contours have not been redrawn or transferred to a label and thus the risk of inaccuracies is decreased. Of course it would be possible to record the contours on the device of the invention, cut the aperture in the sheet, place it in correct orientation on the wafer, use the cut-out as a template for redrawing the contours on the wafer, remove the device and cut the wafer after the redrawn contours. However, the method is unnecessarily laborious and the accuracy of the drawing may be decreased.

The adhesive wafer of an appliance for ostomy, fistula, wound or drain site treatment may be made from any appropriate skin friendly material known per se for the purpose and may also comprise a top film known per se. The skin-friendly adhesive may be any skin-friendly adhesive known per se, e.g. an adhesive comprising hydrocolloids or other moisture absorbing constituents for prolonging the time of use. The appliance may be provided with attachment means for attaching for example an collection bag or a lid and may be a system known per se comprising matching coupling rings or matching flanges and adhesive surfaces.

The appliance may comprise any suitable conventional collection bag known per se.

The also relates to the use of a device according to claim 1 for tracing the contours of a fistulae or wound. Furthermore the invention relates to the use of a device according to claim 1 for tracing the contours of an ostomy.

DESCRIPTION OF THE PREFERRED EMBODIMENTS

The invention is now explained more in detail with reference to the drawings showing preferred embodiments of the invention.

In FIG. 1 is shown a preferred embodiment of the invention. The device comprises a polymer sheet having a first surface facing the wound and a second surface. The second surface is provided with a central, transparent portion (1) with marking for aiding the registration of the wound or opening, in the form of a bulls-eye grid, and indications (2) securing the orientation of the device is proper. Furthermore, the surface is provided with an adhesive border (3) for securing the device to an appliance. The border portion is not necessarily transparent, it is not of importance whether this portion is transparent or not. The adhesive layer is protected by a large release liner (4) and a small release liner (5). When the small release liner (5) is removed, the exposed adhesive is used for positioning the sheet correctly. When position is proper, the large release liner (4) is removed and the rest of the adhesive layer of the device is adhered to the application.

Figure 2:
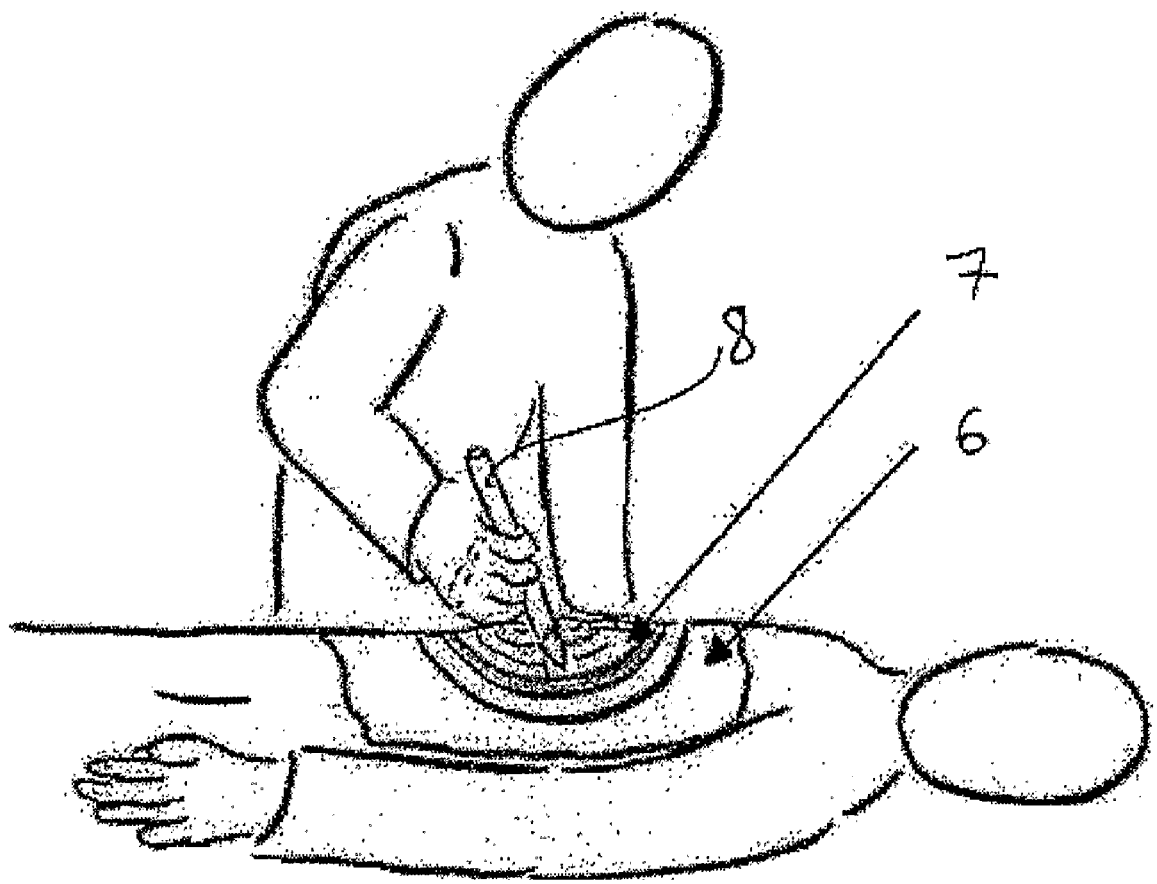
FIG. 2 shows tracing of a wound or opening on the device of the invention.

In FIG. 2 is shown tracing of the contours of a wound. The wound is covered with a transparent protection layer (1) for sanitary precautions and for avoiding exudates on the device of the invention. The device of the invention (2) is placed over the wound or opening with the surface comprising the adhesive border (3) facing away from the wound. The contours are traced with a marking pen (4) on the central portion of the device (2).

Figure 3:
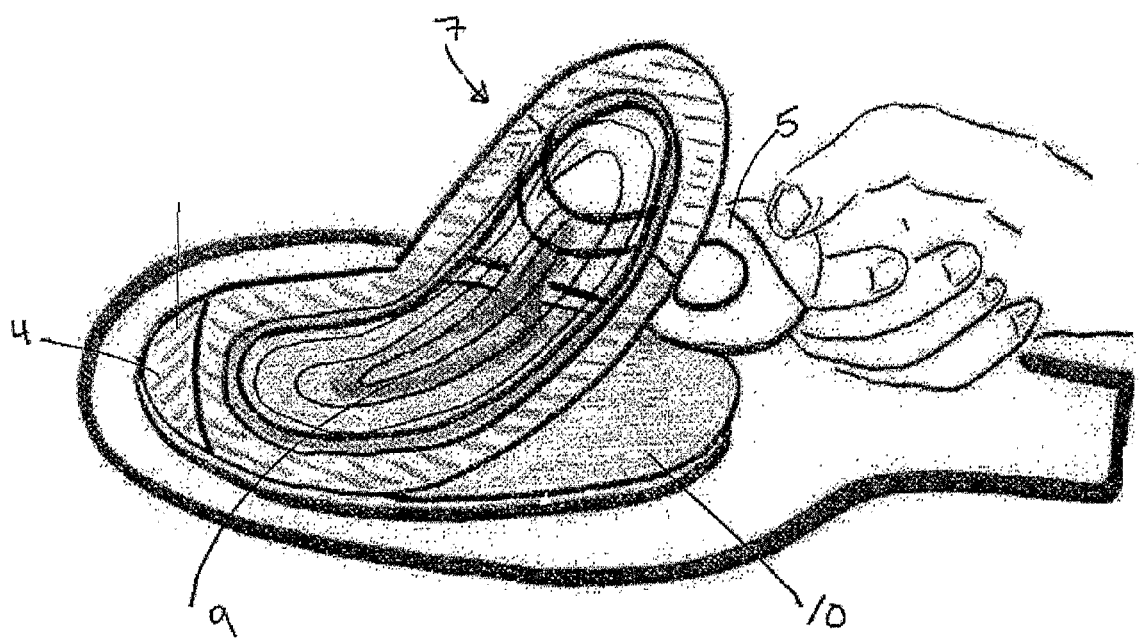
FIG. 3 shows the application of the device of the invention to an appliance and FIG. 4 shows cutting the combined appliance and device.
Figure 4:
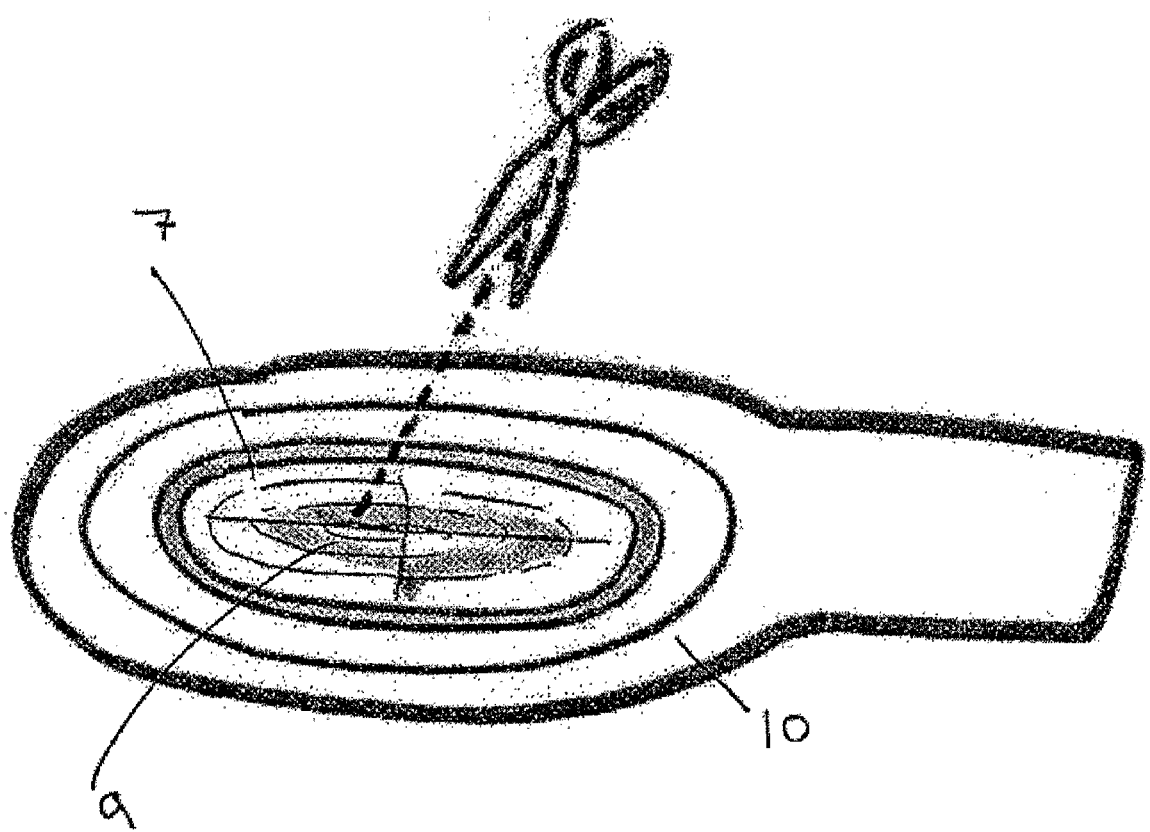

Then the device is removed from the patient, the protection layer is discarded, and the device is reversed, the small release liner (4) is removed, and the device is positioned on the skin-facing surface of an appliance (FIG. 3), the exposed adhesive area fixing the device to the appliance. Then the large release liner (5) is then removed and the device is adhered to the appliance, showing a mirror image of the wound or opening. Finally, the combined appliance and device are cut (FIG. 4) along the traced contours in order to provide an aperture in the adhesive wafer of the appliance for obtaining the wound or opening. Thus the cutting is in the line drawn directly from the wound or opening, the drawing has not been transferred and redrawn. In this manner the accuracy of the cutting is improved and a snug fit to the wound or opening is achieved.

The invention claimed is:

1. A method for recording and transferring the contours of a wound or opening in the tissue of a human being comprising the steps of:
    a) covering the wound or opening with a transparent polymer sheet having a first and a second surface, wherein the first surface faces the wound or opening and the second surface comprises a central portion and an edge portion wherein the edge portion is provided with an adhesive layer,
    b) tracing the contours of the wound or opening on the central portion of the second surface of the sheet,
    c) removing the sheet from the wound or opening,
    d) attaching the adhesive layer of the second surface of the sheet to the skin-facing surface of an adhesive wafer of an appliance for ostomy, fistula, wound or drain site treatment,
    e) cutting an aperture in the adhesive wafer for receiving the wound or opening.

2. A method according to claim 1 wherein the transparent polymer sheet is removed from the wafer after cutting and saved for the patients record.

3. A method according to claim 1 wherein a transparent protection layer is placed between the wound and the transparent sheet.

4. A method according to claim 2 wherein the transparent protection sheet is attached to the first surface of the transparent polymer sheet.

5. A method according to claim 1 comprising tracing the contours of a fistulae.

6. A method according to claim 1 comprising tracing the contours of an ostomy.

7. A method according to claim 1 wherein cutting an aperture in the adhesive wafer for receiving the wound or opening comprises cutting a mirror image aperture into an adhesive side of the adhesive wafer, the method further comprising:
    turning the adhesive side of the adhesive wafer over, thus turning over the mirror image aperture cut into the adhesive wafer, and applying the adhesive side of the adhesive wafer to the wound or opening such that the adhesive wafer fits the contours of the wound or opening.

* * * * *